United States Patent [19]

Mar et al.

[11] Patent Number: 4,721,117

[45] Date of Patent: Jan. 26, 1988

[54] TORSIONALLY STABILIZED GUIDE WIRE WITH OUTER JACKET

[75] Inventors: Craig E. Mar, Fremont; Lambert J. Diettrich, Danville; David W. Morrison, San Jose, all of Calif.

[73] Assignee: Advanced Cardiovascular Systems, Inc., Mountain View, Calif.

[21] Appl. No.: 856,492

[22] Filed: Apr. 25, 1986

[51] Int. Cl.⁴ .............................................. A61B 5/00
[52] U.S. Cl. .................................. 128/772; 604/164; 604/170; 604/282
[58] Field of Search .............. 128/657, 772; 604/95, 604/164, 166, 170, 280, 282

[56] References Cited

U.S. PATENT DOCUMENTS

| | | | |
|---|---|---|---|
| 3,789,841 | 2/1974 | Antoshkin | 128/772 |
| 4,538,622 | 9/1985 | Samson et al. | 128/657 |
| 4,554,929 | 11/1985 | Samson et al. | 128/657 |
| 4,619,274 | 10/1986 | Morrison | 128/657 |

Primary Examiner—William E. Kamm
Assistant Examiner—Randy Citrin
Attorney, Agent, or Firm—Fulwider, Patton, Rieber, Lee & Utecht

[57] ABSTRACT

Torsionally stabilized guide wire for use in larger vessels of the vascular system. A relatively flexible helical coil is positioned over the distal end portion of an elongated shaft which increases in flexibility toward its distal end. The coil is affixed to the shaft at the proximal and distal ends of the coil and at an intermediate point near the distal end. A jacket having an outer diameter substantially equal to the outer diameter of the coil covers the shaft between the proximal end of the shaft and the proximal end of the coil. In one disclosed embodiment, the jacket is formed by heat shrinking a tubular sleeve of polyethylene about the shaft.

16 Claims, 1 Drawing Figure

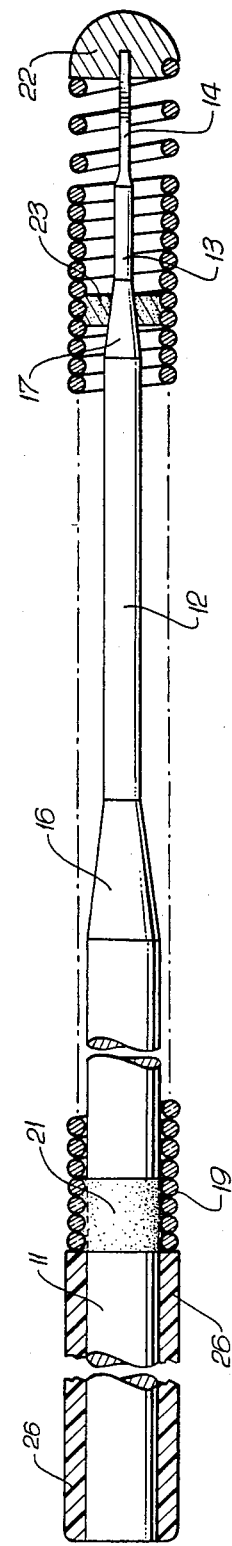

TORSIONALLY STABILIZED GUIDE WIRE WITH OUTER JACKET

This invention pertains generally to the insertion of elements such as catheters into the vascular system, and more particularly to a guide wire and method of manufacturing the same for use in larger vessels as, for example, in the arms, the legs and the carotid arteries.

Guide wires employed in coronary angioplasty are of relatively small diameter because of the relatively small size of the blood vessels and the luminal openings of the dilatation catheters which pass over the guide wires. To facilitate steering or placement within the cardiovascular system, a guide wire should be both relatively flexible toward its distal end and relatively rigid from a torsional standpoint over its entire length. These two desirable properties are somewhat inconsistent and difficult to achieve in practice. Examples of guide wires intended primarily for use in coronary angioplasty are found in U.S. Pat. Nos. 4,554,929 and 4,545,390.

While guide wires designed for coronary angioplasty can, at least in theory, also be employed in the peripheral organs such as the arms and legs, they may not have sufficient torsional rigidity for use in such applications. Another problem with guide wires and dilatation catheters is blood loss between the guide wire and the luminal wall of the catheter. Also, it is difficult to track a catheter with a relatively large luminal opening over a guide wire of relatively small diameter to a desired location. Ideally, the guide wire should fit closely within the luminal opening and loosely enough to permit the catheter to move freely along the wire, a result which is often difficult to achieve in practice.

It is in general an object of the invention to provide a new and improved guide wire.

Another object of the invention is to provide a guide wire in which the guide wire has both high torsional rigidity and good flexibility.

Another object of the invention is to provide a guide wire in which the guide wire fits closely within a dilatation catheter and also allows the catheter to be advanced freely.

Another object of the invention is to provide a guide wire in which the guide wire is particularly suitable for use in larger vessels.

These and other objects are achieved in accordance with the invention by providing a guide wire in which a relatively flexible helical coil is positioned over the distal end portion of an elongated shaft which increases in flexibility toward its distal end. The coil also increases in flexibility toward its distal end and is affixed to the shaft at its proximal and distal ends and at an intermediate point near the distal end. Between the proximal end of the shaft and the proximal end of the coil, the shaft is covered with a jacket having an outer diameter substantially equal to the outer diameter of the coil. In one disclosed embodiment, the jacket is formed by heat shrinking a tubular sleeve of polyethylene about the shaft.

The single FIGURE of drawing is an enlarged, fragmented longitudinal sectional view of one embodiment of a guide wire according to the invention.

The guide wire comprises an elongated mandrel or shaft 11 having a relatively rigid proximal end portion and a relatively flexible distal end portion. The distal end portion increases in flexibility toward the distal end. In the embodiment illustrated, the shaft has a generally circular cross-section, and the distal end portion has sections 12, 13 of progressively smaller diameter and a flattened tip section 14 of generally rectangular cross-section. Relatively short conically tapered sections 16, 17 provide smooth transitions between the sections of different diameter. Alternatively, the distal end portion can have a single continuous taper rather than a series of discrete steps in diameter.

In one presently preferred embodiment, the shaft comprises a stainless steel wire which is ground by a centerless grinding process to form the sections of different diameter. Flattened section 14 is formed by rolling the distal tip of the wire after it is ground to the diameter of section 13.

The dimensions of the shaft are selected to provide the desired properties for the guide wire. The proximal end portion is generally on the order of 10–30% of the overall length of the shaft. In one example of a guide wire for use in the peripheral organs, the proximal end of the shaft has a diameter of 0.020 inch, section 12 has a diameter of 0.013 inch, section 13 has a diameter of 0.004 inch, and section 14 has a thickness of 0.002 inch. In this example, the shaft has an overall length on the order of 145–150 cm, section 12 has a length of about 12 cm, section 13 has a length of about 2 cm, and section 14 has a length of about 3 cm. Each of the transitional sections 16, 17 has a length of about 3–6 cm. For a more flexible guide wire, one or more of the sections can be reduced in diameter, or one of the sections of smaller diameter can be increased in length.

The properties of the guide wire can also be changed by employing a greater or lesser number of sections in the distal end portion of the shaft. For example, a section having a diameter of 0.015 inches might be added between the proximal end portion and section 12 in the example given above. This additional section might, for example, have a length on the order of 25 cm.

A relatively flexible helical coil 19 is positioned coaxially of the distal end portion of the shaft. The coil extends from a point prior to the midpoint of the shaft to the distal end of the shaft. The proximal end of the coil is affixed to the shaft by suitable means such as a band of cyanoacrylate adhesive 21, and the distal end of the coil is affixed to the distal end of the shaft. A tip 22 of radiopaque material such as gold is provided at the distal end of the coil, and in the embodiment illustrated, the distal ends of the coil and shaft are held together by the opaque material.

In one presently preferred embodiment, coil 19 is fabricated of a stainless steel wire coated with Teflon. The inside diameter of the coil corresponds to the diameter of the proximal end portion of shaft 11, and with a 0.020 inch shaft, the coil typically has an outside diameter of 0.035 inch. The windings of the coil are closely spaced except in the vicinity of tip section 14 where they are spread apart for increased flexibility and easier shaping. The spread portion of the windings extends about 2.5–3.5 cm back from tip 22 and is aligned with the flattened tip section 14 of the shaft or core 11.

Helical coil 19 is also affixed to shaft 11 at an intermediate point 23 near the distal end of the shaft. Point 23 is spaced a short distance (e.g., 7–8 cm) from the distal end, and the connection between the coil and shaft at this point is made by suitable means such as brazing. This connection gives the coil an increased torsional rigidity and isolates the tip portion from the main body of the wire for greater flexibility when sharp bends are encountered.

A tubular sleeve or jacket 26 is mounted on shaft 11 between the proximal end of the shaft and the proximal end of coil 19. This sleeve is preferably fabricated of a heat shrinkable material such as polyethylene or Teflon, and it is shrunk tightly about the shaft. The outside diameter of the jacket is substantially equal to the outside diameter of the coil, thereby giving the jacket a thickness substantially equal to the thickness of the wire forming the coil, so that the guide wire has a substantially uniform diameter throughout its entire length. In a guide wire having an overall length of 145 cm, the jacket might be 45 cm long, and the coil might be 100 cm, with the distal end of the jacket abutting against the proximal end of the coil.

If desired, the tip portion of the guide wire beyond point 23 can be bent to a desired shape to facilitate steering of the guide wire.

In a presently preferred method of manufacture, shaft 11 is ground and rolled to the desired configuration. The heat shrinkable material is placed on the proximal end of shaft 11 and shrunk tightly about the shaft to form jacket 26. Coil 19 is coated with Teflon and placed over the distal end portion of the shaft. The proximal end of the coil is affixed to the shaft by cyanoacrylate adhesive 21, and the distal ends of the coil and shaft are brazed together with the radiopaque material which forms tip 22. The coil and shaft are also brazed together at the intermediate point 23.

The guide wire has a number of important features and advantages. It has a relatively high torsional rigidity and a flexible tip which is isolated from the main body of the wire. This facilitates steering and placement of the wire in the vascular system. The wire has a substantially uniform diameter throughout its entire length, and this minimizes blood loss between the wire and the luminal wall of a catheter advanced along the wire. The jacket on the proximal end of the shaft reduces friction and enhances the appearance of the guide wire.

It is apparent from the foregoing that a new and improved guide wire and method of manufacturing the same have been provided. While only certain presently preferred embodiments have been described in detail, as will be apparent to those familiar with the art, certain changes and modifications can be made without departing from the scope of the invention as defined by the following claims.

We claim:

1. In a guide wire for use in the vascular system: an elongated shaft having a relatively flexible distal end portion, a helical coil extending over the distal end portion of the shaft and a substantial portion of the shaft proximal to the relatively flexible distal end portion, said helical coil being affixed to the shaft at its ends and at a point between its ends, and a jacket of polyethylene heat shrunk about the shaft proximally of the helical coil and having a thickness corresponding to the thickness of the wire which forms the coil and an outer diameter substantially equal to the outer diameter of the coil.

2. The guide wire of claim 1 including a tip of radiopaque material at the distal end of the shaft.

3. The guide wire of claim 1 wherein the helical coil is coated with Teflon.

4. The guide wire of claim 1 wherein the distal end portion of the shaft decreases in cross-sectional dimension toward the distal end of the shaft.

5. The guide wire of claim 4 wherein the cross-sectional dimension of the distal end portion decreases in discrete steps.

6. The guide wire of claim 1 wherein the windings toward the distal end of the coil are spread apart for greater flexibility and ease of shaping.

7. The guide wire of claim 1 wherein one end of the coil is bonded to the shaft by a cyanoacrylate adhesive.

8. In a guide wire for use in the vascular system: an elongated shaft having a distal end portion of progressively smaller cross-sectional dimension and increasing flexibility extending for a distance on the order of 10–30% of the length of the shaft, a relatively flexible helical coil positioned coaxially of the shaft and extending from a point proximal to the midpoint of the shaft to the distal end of the shaft with the ends of the coil being affixed to the shaft, and a tubular jacket covering the shaft proximally of the coil and having a thickness substantially equal to the thickness of the wire forming the coil and an outer diameter substantially equal to the outer diameter of the coil.

9. The guide wire of claim 8 wherein the helical coil is also affixed to the shaft at a point between the ends of the coil.

10. The guide wire of claim 8 including a tip of radiopaque material at the distal end of the shaft.

11. The guide wire of claim 8 wherein the tubular jacket is fabricated of a polyethylene tubing which is heat shrunk about the shaft.

12. The guide wire of claim 8 wherein the tubular jacket is fabricated of Teflon.

13. The guide wire of claim 8 wherein the helical coil is coated with Teflon.

14. The guide wire of claim 8 wherein the distal end portion of the shaft has a plurality of sections of progressively smaller diameter, and a flattened tip portion of rectangular cross-section.

15. The guide wire of claim 8 wherein the windings of the coil toward the distal end of the shaft are spread apart for greater flexibility and ease of shaping.

16. The guide wire of claim 8 wherein the proximal end portion of the coil is bonded to the shaft by a cyanoacrylate adhesive.

* * * * *